US00PP09570P

United States Patent [19]

Hrebeniuk

[11] Patent Number: Plant 9,570

[45] Date of Patent: Jun. 4, 1996

[54] POINSETTIA PLANT NAMED 'NUTCRACKER WHITE'

[75] Inventor: Alexander Hrebeniuk, Sugar Run, Pa.

[73] Assignee: Oglevee, Ltd., Connellsville, Pa.

[21] Appl. No.: 393,855

[22] Filed: Feb. 24, 1995

[51] Int. Cl.[6] ..... A01H 5/00

[52] U.S. Cl. ..... Plt./86.2

[58] Field of Search ..... Plt./86.2

[56] References Cited

U.S. PATENT DOCUMENTS

P.P. 9,177 6/1995 Hrebeniuk ..... Plt./86.4

OTHER PUBLICATIONS

Sigurbjörnsson, B., "Chapter B Induced Mutations" *Crop Breeding* 1983 ASACSSA, Madison, WI pp. 153–176.

*Primary Examiner*—James R. Feyrer

*Attorney, Agent, or Firm*—Webb Ziesenheim Bruening Logsdon Orkin & Hanson

[57] ABSTRACT

A poinsettia plant named "Nutcracker White" particularly characterized by its white, multiple layered, and non-drooping bracts having a broad base and an above average number of long lasting cyathia which are held tightly together on short stalks.

1 Drawing Sheet

BACKGROUND OF THE NEW PLANT

The present invention comprises a new and distinct cultivar or *Euphorbia pulcherrima* known by the varietal name "Nutcracker White".

The new cultivar was discovered in a planned mutation program of variety H-327 (which is the subject matter of Plant patent application Ser. No. 08/257,102, now U.S. Plant Pat. No. 9,177) in November of 1993 in Sugar Run, Pa. During the mutation program, unrooted cuttings were subjected to 4,000 rads of gamma rays at Penn State Brazelle Nuclear Reactor (cobalt 60, 1.25 MEV) for 2½ minutes. The new cultivar was first asexually reproduced by cuttings in June of 1994 in Sugar Run, Pa. and has been repeatedly asexually reproduced by cuttings at Sugar Run, Pa. Continued observations from the vegetative cuttings have confirmed that the distinguishing features of this new cultivar come true, remain stable and are retained through successive propagations.

The following traits are determined to be basic characteristics of this new cultivar which in combination distinguish this poinsettia as new and distinct:

1. Color is whiter, less green and yellow than commercial varieties.

2. The bracts have more layers which are spaced further apart than commercial varieties, a broad base and is non-drooping.

3. An above average number of cyathia, which are held tightly together on short stalks and are long lasting.

The new cultivar differs from its parent essentially only in the bract coloration.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Sugar Run, Pa. The color readings were determined under cool white light (150 F.C.) at 10:00 a.m. on Dec. 14, 1994 at Connellsville, Pa. Color references are primarily to the R.H.S. Colour Chart of The Royal Horticultural Society of London.

The plant:

*Branching.*—Self branching.

*Rooting.*—Fast.

*Blooming habit.*—8½ week response.

*Blooming season.*—Plant is saleable 6 weeks from initiation.

*Height.*—Up to 18" on a single stem and 10" to 12" on a pinched stem.

Foliage:

*Size.*—Medium — old leaves ovate; middle leaves with dentate margin.

*Quantity.*—Average, up to 16 leaves per stem.

*Color.*—New foliage — Upper side, Green Group 137 A. Under side, Green Group 138 B. Old foliage — Upper side, Green Group 137 A. Under side, Green Group 138 B. Leaf petiole — Yellow-Green Group 146 D.

*Shape.*—Ovate.

*Texture.*—Veins slightly pronounced; "V" shaped ripples.

*Edge of margin.*—Dentate, only on middle leaves.

*Aspect.*—Medium green in color and slightly drooped.

*Veins.*—Location — Pinnate. Color — Yellow-Green Group 147 C.

Flower:

*Quantity.*—Above average, 12–14 cyathia.

*Number of nectaries.*—Above average.

*Size.*—Average.

*Color.*—Green with bright lemon yellow cyathia.

Bracts:

*Size.*—Layer is 12" to 16" in diameter; individual bracts are 3" to 4" wide by 5" to 7" long.

*Number of layers.*—Three.

*Quanity.*—20 to 25 bracts.

*Shape.*—Ovate.

*Color.*—Yellow Group 8 D.

*Margin.*—Dentate, only on middle leaves.

*Veins.*—Location — Pinnate. Color — Yellow-Green Group 145 C.

Reproductive organs: Typical for poinsettia cultivars.

*Stamens.*—Number — 20 to 30. Color — White.
*Pollen color.*—Lemon Yellow.
*Style color.*—Yellow-Green Group 146 B.
*Ovary color.*—Yellow-Green Group 146 D.
*Nectar cup color.*—Yellow Group 13 C.

I claim:

1. A new and distinct variety of poinsettia plant as herein shown and described, particularly characterized by its triple form, broad base, large flower, long lasting, tightly held cyathia and non-drooping, multi-layered white bracts.

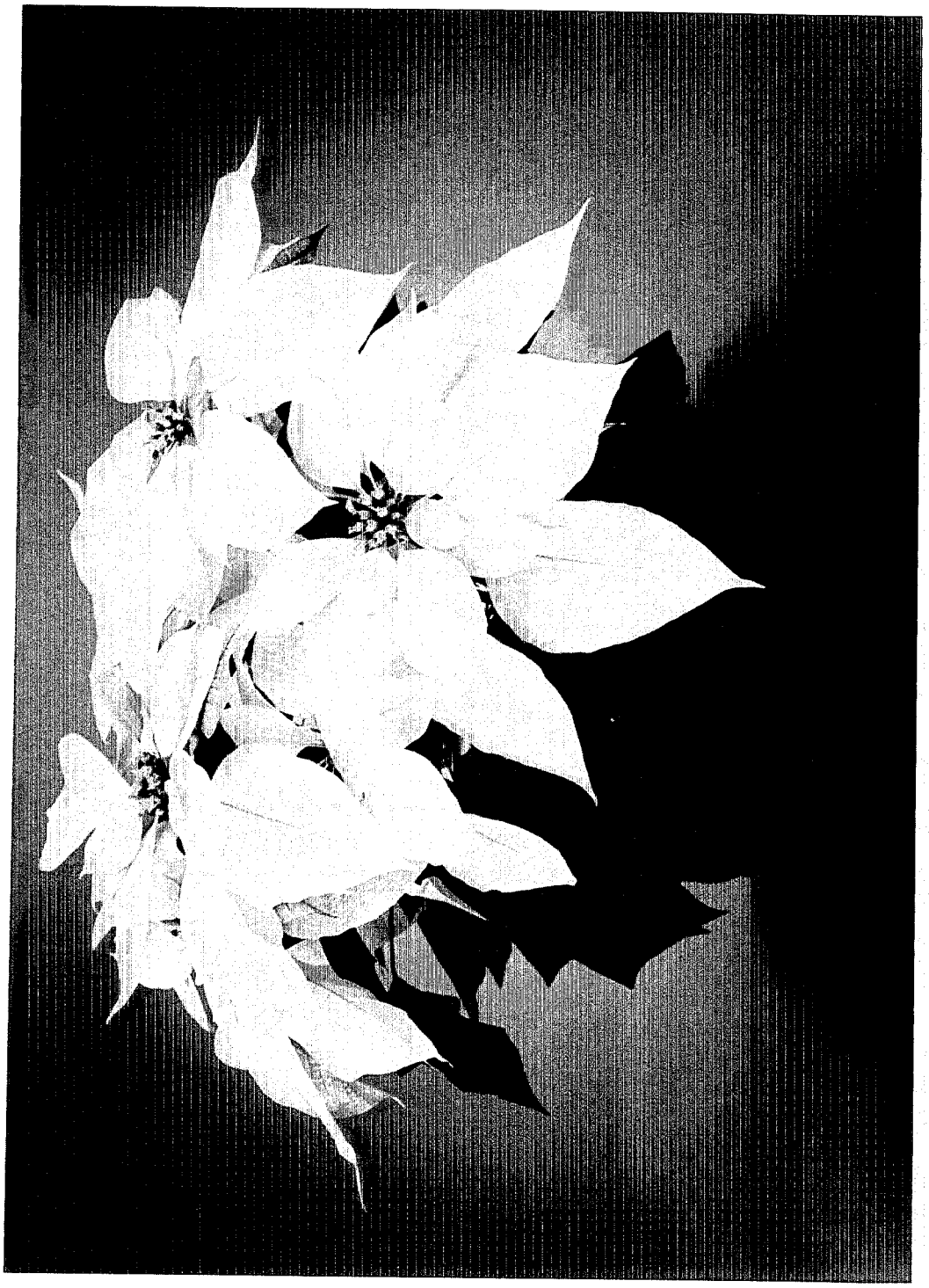

* * * * *